US008784867B2

(12) United States Patent
Samuel et al.

(10) Patent No.: US 8,784,867 B2
(45) Date of Patent: Jul. 22, 2014

(54) CONTACT LENSES CONTAINING CAROTENOID AND METHOD FOR MAKING SAME

(71) Applicant: Novartis AG, Basel (CH)

(72) Inventors: Newton T. Samuel, Suwanee, GA (US); Nirupama Kenkare, Alpharetta, GA (US); Peter D. Lackey, Snellville, GA (US); Jessie Chen, Duluth, GA (US)

(73) Assignee: Novartis AG, Basel (CH)

( * ) Notice: Subject to any disclaimer, the term of this patent is extended or adjusted under 35 U.S.C. 154(b) by 25 days.

(21) Appl. No.: 13/716,496

(22) Filed: Dec. 17, 2012

(65) Prior Publication Data

US 2013/0178518 A1   Jul. 11, 2013

Related U.S. Application Data

(60) Provisional application No. 61/578,562, filed on Dec. 21, 2011.

(51) Int. Cl.
| | | |
|---|---|---|
| *A61K 9/00* | (2006.01) | |
| *G02B 1/04* | (2006.01) | |
| *A61K 31/355* | (2006.01) | |
| *C07C 403/24* | (2006.01) | |
| *A61F 9/00* | (2006.01) | |
| *C09B 61/00* | (2006.01) | |

(52) U.S. Cl.
CPC .............. *A61K 9/0051* (2013.01); *G02B 1/043* (2013.01); *A61K 31/355* (2013.01); *C07C 403/24* (2013.01); *A61F 9/0017* (2013.01); *C09B 61/00* (2013.01)
USPC ............................ 424/429; 514/458; 585/351

(58) Field of Classification Search
None
See application file for complete search history.

(56) References Cited

U.S. PATENT DOCUMENTS

| | | | |
|---|---|---|---|
| 6,367,929 B1 | 4/2002 | Maiden | |
| 6,451,871 B1 | 9/2002 | Winterton | |
| 6,627,124 B1 | 9/2003 | Herbrechtsmeier | |
| 6,719,929 B2 | 4/2004 | Winterton | |
| 6,793,973 B2 | 9/2004 | Winterton | |
| 6,811,805 B2 | 11/2004 | Gilliard | |
| 6,822,016 B2 | 11/2004 | McCabe | |
| 6,896,926 B2 | 5/2005 | Qiu | |
| 7,875,660 B2 | 1/2011 | Winterton | |
| 7,968,050 B2 | 6/2011 | Vogt | |
| 2006/0100408 A1 | 5/2006 | Powell | |
| 2006/0251696 A1 | 11/2006 | Winterton | |
| 2010/0140114 A1 | 6/2010 | Pruitt | |
| 2010/0330146 A1 | 12/2010 | Chauhan | |

FOREIGN PATENT DOCUMENTS

| | | |
|---|---|---|
| EP | 1611877 A1 | 1/2006 |
| WO | 2009084069 A2 | 7/2009 |
| WO | 2009094466 A2 | 7/2009 |

OTHER PUBLICATIONS

PCT International Search Report dated Mar. 11, 2013, International Application No. PCT/US20121070037, International Filing Date Dec. 17, 2012.
PCT Written Opinion of the International Searching Authority dated Mar. 11, 2013, International Application No. PCT/US2012/070037, International Filing Date Dec. 17, 2012.
Authors: Cheng-Chun Peng, Jinah Kim, Anuj Chauhan Article: Extended delivery of hydrophilic drugs from silicone-hydrogel contact lenses containing vitamin E diffusion barriers. Published: Biomaterials vol. 31, 2010 pp. 4032-4047.

*Primary Examiner* — Bethany Barham

(74) *Attorney, Agent, or Firm* — Sheng-Hsin Hu

(57) ABSTRACT

The instant invention pertains to a method for producing contact lenses with improved oxidative stability of Carotenoids in the contact lens. The method of the invention involves adding a vitamin E material into a contact lens in an amount sufficient to reduce oxidative degradation of Carotenoids in the lens by at least about 30% in comparison with an identical contact lens without the vitamin E material.

14 Claims, No Drawings

CONTACT LENSES CONTAINING CAROTENOID AND METHOD FOR MAKING SAME

This application claims the benefit under 35 USC §119 (e) of U.S. provisional application Ser. No. 61/578,562 filed Dec. 21, 2011, incorporated herein by reference in its entirety.

The present invention is related to a contact lens containing carotenoid and vitamin E material with enhancement of oxidative stability of carotenoid during lens autoclave and/or lens storage. The present invention is also related to a method for making a contact lens containing Carotenoids and vitamin E, thereby enhancing the oxidative stability of carotenoids during lens autoclave and/or lens storage.

BACKGROUND

Carotenoid molecules have multiple potential uses when loaded into contact lenses due to their anti-oxidant and other properties; possibilities include comfort agents, general ocular health, specific treatment for eye diseases such as AMD (age-related macular degeneration), or simply to signal the depletion of a co-eluting comfort molecule. Carotenoid molecules can also be used in the preparation of blue-light absorbing contact lenses.

However, the extended unsaturation present in the carotenoid chemical structure makes Carotenoid susceptible to oxidative damages during lens autoclave and/or lens storage.

Therefore, there is a need for a process for cast-molding contact lenses with an enhanced the oxidative stability of carotenoids during lens autoclave and/or lens storage.

SUMMARY OF THE INVENTION

The invention, in one aspect, provides a method for preparing a contact lens, comprising the steps of:

(a) obtaining a contact lens, (b) immersing the contact lens in a solution containing a carotenoid and a vitamin E material for a period of time sufficient to load a desired amount of a carotenoid and a vitamin Ematerial; and (c) autoclaving the contact lens of step (b) to sterilize the contact lens, wherein the contact lens has a lower oxidative degradation of carotenoids during lens autoclave and/or lens storage by at least about 30% in comparison to an identical contact lens without the vitamin E material.

The invention, in another aspect, provides a contact lens, comprising: a formed water swellable, polymeric lens body; a carotenoids and a vitamin E material, wherein the vitamin E material is present in an amount sufficient to reduce oxidative degradation of the carotenoids during lens autoclave and/or lens storage by at least about 30% in comparison to an identical contact lens without the vitamin E material.

DETAILED DESCRIPTION OF THE PREFERRED EMBODIMENTS

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. The singular forms "a", "an" and "the" include plural aspects unless the context clearly dictates otherwise. Thus, for example, reference to a phospholipid includes a single phospholipid, as well as two or more phospholipids. The nomenclature used herein and the laboratory procedures described below are those well known and commonly employed in the art. As employed throughout the disclosure, the following terms, unless otherwise indicated, shall be understood to have the following meanings.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

The "front or anterior surface" of a contact lens, as used herein, refers to the surface of the lens that faces away from the eye during wear. The anterior surface, which is typically substantially convex, may also be referred to as the front curve of the lens.

The "rear or posterior surface" of a contact lens, as used herein, refers to the surface of the lens that faces towards the eye during wear. The rear surface, which is typically substantially concave, may also be referred to as the base curve of the lens.

A "hydrogel" or "hydrogel material" refers to a polymeric material which can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

"Hydrophilic," as used herein, describes a material or portion thereof that will more readily associate with water than with lipids.

A "monomer" means a low molecular weight compound that can be polymerized and comprises one or more actinically crosslinkable groups. Low molecular weight typically means average molecular weights less than 700 Daltons.

An "actinically-crosslinkable group" refers to a group which can react with another group of same type or different type to form a covalent linkage upon actinic irradiation. Examples of actinically-crosslinkable groups include without limitation acryl groups, thiol groups, and ene-containing groups. Acryl groups can undergo free-radical chain reaction upon actinic irradiation. Thiol groups (—SH) and ene-containing groups can participate in thiol-ene step-growth radical polymerization as described in a commonly-owned copending U.S. patent application No. 60/869,812 filed Dec. 13, 2006 (entitled "PRODUCTION OF OPHTHALMIC DEVICES BASED ON PHOTO-INDUCED STEP GROWTH POLYMERIZATION"), herein incorporated in reference in its entirety.

An "acryl group" is an organic radical having a formula of

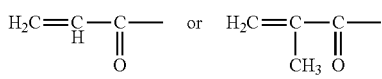

provided the carbonyl is connected to O or N.

A "ene-containing group" is a mono-valent or divalent radical contains a carbon-carbon double which is not directly linked to a carbonyl group (—CO—), nitrogen atom, or oxygen atom and is defined by any one of formula (I)-(III)

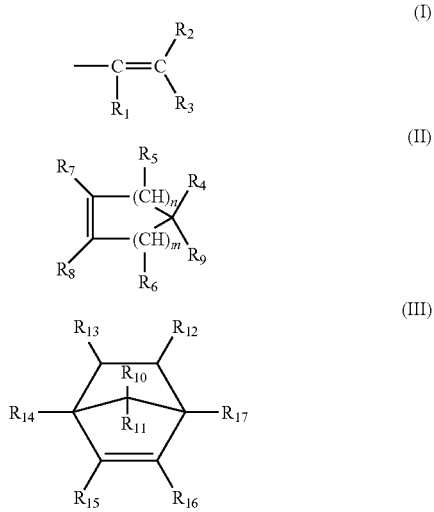

in which $R_1$ is hydrogen, or $C_1$-$C_{10}$ alkyl; $R_2$ and $R_3$ independent of each other are hydrogen, $C_1$-$C_{10}$ alkene divalent radical, $C_1$-$C_{10}$ alkyl, or —$(R_{18})_a$—$(X_1)_b$—$R_{19}$ in which $R_{18}$ is $C_1$-$C_{10}$ alkene divalent radical, $X_1$ is an ether linkage (—O—), a urethane linkage (—N), a urea linkage, an ester linkage, an amid linkage, or carbonyl, $R_{19}$ is hydrogen, a single bond, amino group, carboxylic group, hydroxyl group, carbonyl group, $C_1$-$C_{12}$ aminoalkyl group, $C_1$-$C_{18}$ alkylaminoalkyl group, $C_1$-$C_{18}$ carboxyalkyl group, $C_1$-$C_{18}$ hydroxyalkyl group, $C_1$-$C_{18}$ alkylalkoxy group, $C_1$-$C_{12}$ aminoalkoxy group, $C_1$-$C_{18}$ alkylaminoalkoxy group, $C_1$-$C_{18}$ carboxyalkoxy group, or $C_1$-$C_{18}$ hydroxyalkoxy group, a and b independent of each other is zero or 1, provided that only one of $R_2$ and $R_3$ is a divalent radical; $R_4$-$R_9$, independent of each other, are hydrogen, $C_1$-$C_{10}$ alkene divalent radical, $C_1$-$C_{10}$ alkyl, or —$(R_{18})_a$—$(X_1)_b$—$R_{19}$, provided that only one or two of $R_4$-$R_9$ are divalent radicals; n and m independent of each other are integer number from 0 to 9, provided that the sum of n and m is an integer number from 2 to 9; $R_{10}$-$R_{17}$, independent of each other, are hydrogen, $C_1$-$C_{10}$ alkene divalent radical, $C_1$-$C_{10}$ alkyl, or —$(R_{18})_a$—$(X_1)_b$—$R_{19}$, provided that only one or two of $R_{10}$-$R_{17}$ are divalent radicals.

A "vinylic monomer", as used herein, refers to a monomer that has an ethylenically unsaturated group and can be polymerized actinically or thermally.

The term "olefinically unsaturated group" or "ethyltenically unsaturated group" is employed herein in a broad sense and is intended to encompass any groups containing a >C=C< group. Exemplary ethylenically unsaturated groups include without limitation acryloyl, methacryloyl, allyl, vinyl, styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

A "hydrophilic monomer" refers to a monomer which can be polymerized to form a polymer that is water-soluble or can absorb at least 10 percent by weight of water.

A "hydrophobic monomer", as used herein, refers to a monomer which is polymerized to form a polymer that is insoluble in water and can absorb less than 10 percent by weight water.

A "macromer" refers to a medium and high molecular weight compound which can be polymerized and/or crosslinked and comprise one or more actinically-crosslinkable groups. Medium and high molecular weight typically means average molecular weights greater than 700 Daltons.

A "prepolymer" refers to a starting polymer which contains actinically crosslinkable groups and can be cured (e.g., crosslinked) actinically to obtain a crosslinked polymer having a molecular weight much higher than the starting polymer.

A "silicone-containing prepolymer" refers to a prepolymer which contains silicone and can be crosslinked actinically to obtain a crosslinked polymer having a molecular weight much higher than the starting polymer.

"Molecular weight" of a polymeric material (including monomeric or macromeric materials), as used herein, refers to the number-average molecular weight unless otherwise specifically noted or unless testing conditions indicate otherwise.

"Polymer" means a material formed by polymerizing one or more monomers.

As used herein, the term "multiple" refers to three or more.

A "photoinitiator" refers to a chemical that initiates radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types, and Irgacure® types, preferably Darocure® 1173, and Irgacure® 2959.

A "thermal initiator" refers to a chemical that initiates radical crosslinking/polymerizing reaction by the use of heat energy. Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(isobutyronitrile) (AIBN).

A "spatial limitation of actinic radiation" refers to an act or process in which energy radiation in the form of rays is directed by means of, for example, a mask or screen or combinations thereof, to impinge, in a spatially restricted manner, onto an area having a well defined peripheral boundary. For example, a spatial limitation of UV radiation can be achieved by using a mask or screen which has a transparent or open region (unmasked region) surrounded by a UV impermeable region (masked region), as schematically illustrated in FIGS. 1-9 of U.S. Pat. No. 6,627,124 (herein incorporated by reference in its entirety). The unmasked region has a well defined peripheral boundary with the masked region.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting a lens.

"Dye" means a substance that is soluble in a solvent and that is used to impart color. Dyes are typically translucent and absorb but do not scatter light. Any suitable biocompatible dye can be used in the present invention.

A "Pigment" means a powdered substance that is suspended in a liquid in which it is insoluble. A pigment can be a fluorescent pigment, phosphorescent pigment, pearlescent pigment, or conventional pigment. While any suitable pigment may be employed, it is presently preferred that the pigment be heat resistant, non-toxic and insoluble in aqueous solutions.

The term "fluid" as used herein indicates that a material is capable of flowing like a liquid.

"Surface modification", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, mold-transfer coating process disclosed in U.S. Pat. No. 6,719,929 (herein incorporated by reference in its entirety), the incorporation of wetting agents into a lens formulation for making contact lenses proposed in U.S. Pat. Nos. 6,367,929 and 6,822,016 (herein incorporated by references in their entireties), reinforced mold-transfer coating disclosed in U.S. Patent Application No. 60/811,949 (herein incorporated by reference in its entirety), and layer-by-layer coating ("LbL coating") obtained according to methods described in U.S. Pat. Nos. 6,451,871, 6,719,929, 6,793,973, 6,811,805, 6,896,926 (herein incorporated by references in their entirety).

The term "oxidative degradation of Carotenoid" means that the percentage of oxidative degradation of a Carotenoid in a contact lens during an autoclaving treatment or contact lens storage.

The percentage of degradation of Carotenoid during an autoclaving treatment of a contact lens is defined as:

Oxidative degradation of carotenoid of a contact lens=
[(Carotenoid0(µg)−Carotenoid 1(µg)/Carotenoid0(µg)]×100

In which Carotenoid0 (µg) and Carotenoid 1 (µg) represent the amount of Carotenoid present in lens before lens autoclave and after lens autoclave, respectively.

The percentage of degradation of Carotenoid during storage of a contact lens is defined as:

Oxidative degradation of carotenoid of a contact lens=
[(Carotenoid $x$(µg)−Carotenoid $y$(µg)/Carotenoid $x$(µg)]×100

In which Carotenoid x (µg) and Carotenoid y (µg) represent the amount of Carotenoid present in lens at starting time and after storage for a specified period time at a predetermined temperature, respectively.

The invention is partly based on the discovery that, a Vitamine E can be used as a stabilizing agent in a soft hydrogel lens including a Carotenoid to reduce the oxidative degradation during lens autoclave and/or lens storage. The mechanism for Vitamine E worked as a stabilizing agent in a soft hydrogel lens including a Carotenoid is not well understood.

The amount of Vitamine E and Carotenoid can be determined by UV/VIS spectrophotometry.

The invention, in one aspect, provides a method for preparing a contact lens, comprising the steps of:

(a) obtaining a contact lens, (b) immersing the contact lens in a solution containing a carotenoid and a vitamin E material for a period of time sufficient to load a desired amount of a carotenoid and a vitamin E material; and (c) autoclaving the contact lens of step (b) to sterilize the contact lens, wherein the contact lens has a lower oxidative degradation of carotenoids during lens autoclave and/or lens storage by at least about 30% in comparison to an identical contact lens without the vitamin E material.

In accordance with the invention, contact lenses comprising hydrophilic polymeric materials. Such contact lenses are often described as being swellable contact lenses in that during use of such contact lenses the lenses include sufficient amounts of water to be swelled by such water. For example, such contact lenses often include about 10% or about 15% or about 20% to about 50% or about 60% or about 80% by weight of water in an equilibrium state, for example, when being worn on an eye. Such contact lenses are often referred to as soft hydrophilic contact lenses or hydrogel contact lenses. In one particularly useful embodiment, the contact lenses include hydrophilic silicon-containing polymeric materials. The contact lenses to be treated are often produced by copolymerization of a polymerizable composition comprising one or more hydrophilic monomeric materials, at least one silicone-containing monomer or at least one silicone-containing macromer or at least one crosslinkable silicone-containing prepolymer. In accordance with the invention, an hydrogel contact lens can be the hydrogel contact lens with or without surface treatment, but preferably the hydrogel contact lens without surface treatment.

In accordance with the invention, any carotenoid can be used in the invention, so long it can absorb blue light. There are over 600 known carotenoids; they are split into two classes, xanthophylls (which contain oxygen) and carotenes (which are purely hydrocarbons, and contain no oxygen). Carotenoids in general absorb blue light. They serve two key roles in plants and algae: they absorb light energy for use in photosynthesis, and they protect chlorophyll from photodamage. In humans, four carotenoids (beta-carotene, alpha-carotene, gamma-carotene, and beta-cryptoxanthin) have vitamin A activity (meaning they can be converted to retinal), and these and other carotenoids can also act as antioxidants. In the eye, certain other carotenoids (lutein and zeaxanthin) apparently act directly to absorb damaging blue and near-ultraviolet light, in order to protect the macula lutea.

Carotenoids belong to the category of tetraterpenoids (i.e. they contain 40 carbon atoms, being built from four terpene units each containing 10 carbon atoms). Structurally, carotenoids take the form of a polyene hydrocarbon chain which is sometimes terminated by rings, and may or may not have additional oxygen atoms attached.

Carotenoids with molecules containing oxygen, such as lutein and zeaxanthin, are known as xanthophylls.

The unoxygenated (oxygen free) carotenoids such as α-carotene, β-carotene and lycopene are known as carotenes.

Carotenes typically contain only carbon and hydrogen (i.e., are hydrocarbons), and are in the subclass of unsaturated hydrocarbons.

Probably the most well-known carotenoid is the one that gives this second group its name, carotene, found in carrots (also apricots) and are responsible for their bright orange colour. Crude palm oil, however, is the richest source of carotenoids in nature in terms of retinol (provitamin A) equivalent. Vietnamese Gac fruit contains the highest known concentration of the carotenoid lycopene.

Their colour, ranging from pale yellow through bright orange to deep red, is directly linked to their structure. Xanthophylls are often yellow, hence their class name. The double carbon-carbon bonds interact with each other in a process called conjugation, which allows electrons in the molecule to move freely across these areas of the molecule. As the number of double bonds increases, electrons associated with conjugated systems have more room to move, and require less energy to change states. This causes the range of energies of light absorbed by the molecule to decrease. As more frequencies of light are absorbed from the short end of the visible spectrum, the compounds acquire an increasingly red appearance.

Carotenoid can also artificial synthesis. For example, microorganisms (using patented gene sequences) can be used to produce C40 carotenoids that are more pure than naturally derived carotenoids. These include lycopene and beta carotene A Carotenoids used for the present invention may be any natural or synthetic Carotenoid, for example, but are not limited to, Beta-Carotene, lycopene, astaxanthin and Lutein. The preferred Carotenoid is Beta-Carotene.

The vitamin E material is soluble in a non-aqueous liquid, for example, an alcohol component, such as that selected from methanol, ethanol, propanol, and the like and mixtures thereof.

In accordance with the invention, the Carotenoids can present in the contact lens in an amount from 0.5 µg to 50 µg depending on the purpose of loading of Carotenoids in the contact lens. For signaling purposes (eg. End of wear indicator) will need about 0.5 µg to 5 µg. However, delivering for therapeutic purposes will need higher levels of loading such as up to 50 µg. Contact lens also becomes intensely colored with high loadings.

In accordance with the invention, the Vitamin E material can be used as a carotenoid stabilizer to reduce carotenoid damage during contact lens autoclaving process or lens storage.

In accordance with the invention, the vitamin E material can be selected from the group consisting of vitamin E, salts of vitamin E, derivatives of vitamin E and mixtures thereof. The vitamin E material is soluble in a non-aqueous liquid, for example, an alcohol component, such as that selected from methanol, ethanol, propanol, and the like and mixtures thereof.

The term vitamin E is used to refer to all tocol and trienol derivatives. The tocols are alpha-, beta-, gamma- and delta-tocopherols and the trienols are alpha-, beta-, gamma- and delta-tocotrienols. All these substances are found in plants and have vitamin E activity, but alpha-tocopherol is the most active form of vitamin E. In the human body, vitamin E is present primarily as alphatocopherol. Vitamin E can be isolated from natural sources (plants, vegetables and meat) or can be made in the laboratory. Therefore, vitamin E is sold commercially as a natural or synthetic preparation. Naturally occurring alpha tocopherol is now referred to as RRR-alpha tocopherol (formerly d-alpha tocopherol), whereas synthetic alpha tocopherol is referred to as all-rac-alpha tocopherol (formerly dl-alpha-tocopherol). The esterified forms of vitamin E such as alpha tocopherol acetate, alpha tocopherol succinate and alpha tocopherol nicotinate are made in the laboratory and are also sold commercially. In accordance with the invention, the Vitamine E material includes vitamin E, salts of vitamin E, derivatives of vitamin E and mixtures thereof.

In accordance with the invention, the vitamin E can present in the 50 µg to 250 µg depending on the purpose of loading of Carotenoids In accordance with the invention, vitamin E and Carotenoid are soluble in a non-aqueous liquid, for example, chloroform, an alcohol component, such as that selected from methanol, ethanol, propanol, and the like and mixtures thereof. The contact lens are immersed in the solution of vitamin E and Carotenoid containing about 0.0005 wt % to 0.1 wt % by weight of Carotenoid and 0.05 wt % to 0.5 wt % of vitamin E. Such immersing occurs at a temperature in a range of about 200 C to 500 C for a period of time from 20 minutes to 240 minutes.

The invention, in another aspect, provides a contact lens, comprising: a formed water swellable, polymeric lens body; a carotenoids and a vitamin E, wherein the vitamin E is present in an amount sufficient to reduce oxidative degradation of the carotenoids during lens autoclave and/or lens storage by at least about 30% in comparison to an identical contact lens without the vitamin E.

The previous disclosure will enable one having ordinary skill in the art to practice the invention. In order to better enable the reader to understand specific embodiments and the advantages thereof, reference to the following examples is suggested.

EXAMPLE 1

Beta-carotene is initially dissolved in chloroform as a 0.1 wt % solution. It was later made into a 0.001 wt % solution in 1-Propanol and used for loading experiments. Uncoated lotrafilcon B lenses are left in this solution for ~1 hr to load Beta-carotene and later they were transferred to DI water for ~5 minutes and immediately autoclaved in PBS. Vitamin E was co-loaded along with Beta-carotene by adding 0.5 wt % to the above Beta-carotene solution in 1-Propanol and the rest of the steps remain the same. Beta-carotene and Vitamin E can be easily quantified and detected using UV-VIS spectroscopy. The co-loading of Vitamin E resulted in ~250 ug of Vitamin E in the final lens along with Beta-carotene.

The results are summarized in the table below. As expected, there is a clear loss in the autoclave for lenses loaded with only Beta-carotene (~55%). The lenses also lost Beta-carotene during storage of the prepared lenses at room temperature. The loss was further aggravated by leaving in an oven at 45 degrees. However, when the lenses were co-loaded with Vitamin E, there is no indication of loss in the autoclave and also upon storage. The lenses also visibly maintained their color during the storage period. The results clearly demonstrate Vitamin E stabilizing the Beta-carotene loaded in the lens and hence a potential method for stabilizing carotenoids in contact lenses from oxidative damage during processing/storage.

TABLE 1

Summary of Beta-Carotene Loading in Lenses
(At least 3 samples were analyzed to determine loading.
The data represent the average ± std. deviation.)

|  | Before Autoclave (μg) | After Autoclave (μg) | Stored at Room Temperature for 1 week (μg) | Stored at 45 deg. for 1 week (μg) |
|---|---|---|---|---|
| Only Beta-Carotene loading | 0.9 ± 0.1 | 0.4 ± 0.1 | 0.2 ± 0.2 | 0.1 |
| Beta-carotene + Vitamin E loaded lenses | 0.8 ± 0.1 | 1 ± 0.1 | 1.1 ± 0.1 | 0.9 ± 0.1 |

What is claimed is:

1. A method for preparing a contact lens, comprising the steps of:
 (a) obtaining a contact lens,
 (b) immersing the contact lens in a solution containing a carotenoid and a vitamin E material; for a period of time sufficient to load a desired amount of a carotenoid and a vitamin E material; and
 (c) autoclaving the contact lens of step (b) to sterilize the contact lens, wherein the contact lens has a lower oxidative degradation of carotenoids during lens autoclave and/or lens storage by at least about 30% in comparison to an identical contact lens without the vitamin E material.

2. The method of claim 1 wherein the contact lens comprises a hydrophilic silicon-containing polymer.

3. The method of claim 1 wherein the vitamin E material is selected from the group consisting of vitamin E, salts of vitamin E, derivatives of vitamin E and mixtures thereof.

4. The method of claim 1 wherein the carotenoid is selected from the group consisting of Beta-Carotene, lycopene, astaxanthin, Lutein and mixtures thereof.

5. The method of claim 1 wherein the carotenoid is Beta-Carotene.

6. The method of claim 1 in step (b) wherein the contact lens are immersed in the solution of vitamin E material and Carotenoid containing about 0.0005 wt % to 0.1 wt % by weight of Carotenoid and 0.05 wt % to 0.5 wt % of vitamin E.

7. The method of claim 1 wherein the contact lens comprises the vitamin E in an amount of from 50 μg to 250 μg and the Carotenoid in an amount of 0.5 μg to 50 μg.

8. A contact lens, comprising: a formed water swellable, polymeric lens body; a carotenoids and a vitamin E material, wherein the vitamin E material is present in an amount sufficient to reduce oxidative degradation of the carotenoids during lens autoclave and/or lens storage by at least about 30% in comparison to an identical contact lens without the vitamin E material.

9. The contact lens of claim 8, wherein polymeric lens body comprises a hydrophilic silicon-containing polymer.

10. The contact lens of claim 8, wherein the vitamin E material is selected from the group consisting of vitamin E, salts of vitamin E, derivatives of vitamin E and mixtures thereof.

11. The contact lens of claim 8, wherein the carotenoid is selected from the group consisting of Beta-Carotene, lycopene, astaxanthin, Lutein and mixtures thereof.

12. The contact lens of claim 9 wherein the carotenoid is Beta-Carotene.

13. The contact lens of claim 8, wherein the contact lens comprises the vitamin E in an amount of from 50 μg to 250 μg and carotenoid in an amount of from 0.5 μg to 50 μg.

14. The contact lens of claim 8, wherein the contact lens comprises carotenoid in an amount of from 0.5 μg to 5 μg.

* * * * *